(12) United States Patent
Agranat et al.

(10) Patent No.: US 8,198,606 B2
(45) Date of Patent: Jun. 12, 2012

(54) CONCURRENT MONITORING OF A PLURALITY OF SAMPLES BY AN ARRAY OF BIOSENSING ELEMENTS

(75) Inventors: Aharon Agranat, Mevasseret Zion (IL); Shimshon Belkin, Kiryat Ono (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 662 days.

(21) Appl. No.: 12/296,766

(22) PCT Filed: Apr. 10, 2007

(86) PCT No.: PCT/IL2007/000449
§ 371 (c)(1),
(2), (4) Date: May 21, 2009

(87) PCT Pub. No.: WO2007/116402
PCT Pub. Date: Oct. 18, 2007

(65) Prior Publication Data
US 2010/0072396 A1   Mar. 25, 2010

Related U.S. Application Data

(60) Provisional application No. 60/790,545, filed on Apr. 10, 2006.

(51) Int. Cl.
*G01N 21/64*   (2006.01)
(52) U.S. Cl. .................................................. 250/459.1
(58) Field of Classification Search ................ 250/459.1
See application file for complete search history.

(56) References Cited

U.S. PATENT DOCUMENTS

| | | | |
|---|---|---|---|
| 6,304,771 B1 | 10/2001 | Yodh et al. | |
| 6,485,703 B1 * | 11/2002 | Cote et al. | 424/9.1 |
| 6,485,905 B2 * | 11/2002 | Hefti | 435/6.11 |

(Continued)

FOREIGN PATENT DOCUMENTS

EP   0 266 881 A2   5/1988

(Continued)

OTHER PUBLICATIONS

Belkin, S. *Microbial whole-cell sensing systems of environmental pollutants.* Current Opinion in Microbiology, 2003, 6:206-212.

(Continued)

*Primary Examiner* — David Porta
*Assistant Examiner* — Hugh H Maupin
(74) *Attorney, Agent, or Firm* — Oliff & Berridge, PLC

(57) ABSTRACT

A system and method are presented for monitoring detectable responses from multiple biosensing elements while in contact with multiple samples located in an array. The system (1000) comprises an exciting unit (100), and a detection unit (120). The exciting unit (100) is configured for producing an array of exciting signals (102) each characterized by a frequency differing from those of the other exciting signals, and exciting a corresponding array of the biosensing elements (110), thereby enabling each biosensing element to generate a response signal (130) tagged by the different frequency. The detection unit (120) comprises a single receiving element associated with said array of biosensing elements (110) and configured for concurrently receiving the multiple response signals and generating a single output signal (140) indicative thereof. The system thereby enables to identify signal parts corresponding to the response signals of the spatially separated biosensing elements.

52 Claims, 4 Drawing Sheets

U.S. PATENT DOCUMENTS

| | | | |
|---|---|---|---|
| 6,673,532 B2 * | 1/2004 | Rao | 435/4 |
| 2003/0072550 A1 | 4/2003 | Sasaura et al. | |
| 2005/0046847 A1 * | 3/2005 | Cromwell et al. | 356/417 |

FOREIGN PATENT DOCUMENTS

| | | |
|---|---|---|
| EP | 1 605 303 A1 | 12/2005 |
| WO | WO 02/14539 A1 | 2/2002 |

OTHER PUBLICATIONS

Daunert, S., et al. *Genetically Engineered Whole-Cell Sensing Systems: Coupling Biological Recognition with Reporter Genes.* Chem. Rev. 2000, 100: 2705-2738.

Kohler, S., et al. *Reporter gene bioassays in environmental analysis (review).* Fresenius J Anal Chem. 2000, 366: 769-779.

Walmsley, R.M., et al. *Yeast Functional Analysis Reports: Green Fluorescent Protein as a Reporter for the DNA Damage-induced Gene RAD54 in Saccharomyces cerevisiae.* Yeast vol. 13: 1535-1545 (1997).

Van Dyk, TK, et al. *LuxArray, a High-Density, Genomewide Transcription Analysis of Escherichia coli Using Bioluminescent Reporter Strains.* Journal of Bacteriology, Oct. 2001, pp. 5496-5505; vol. 183; No. 19.

Hofmeister, R., et al. *Growth and characterization of the perovskite $K_{1-y}Li_yTa_{1-x}Nb_xO_3$:Cu.* Journal of Crystal Growth. 1993, 131: 486-494.

Hofmeister, R, et al. *New Photorefractive Mechanism in Centrosymmetric Crystals: A Strain-Coordinated Jahn-Teller Relaxation.* Physical Review Letters. vol. 69, No. 9. (Aug. 31, 1992).

Agranat, A., et al. *Characterization of a new photorefractive material: $K_{1-y}L_yT_{1-x}N_x$.* Optics Letters. vol. 17, No. 10 (May 15, 1992).

Polyak, B., et al. *Bioluminescent whole cell optical fiber sensor to genotoxicants; system optimization.* Sensors and Actuators B 74 18-26 (2001).

Koehler, S., et al. *Detection of 4-chlorobenzoate using immobilized recombinant Escherichia coli reporter strains.* Sensors and Actuators B 70 139-144 (2000).

Lyngberg, O.K., et al. *Engineering the Microstructure and Permeability of Thin Multilayer Latex Biocatalytic Coatings Containing E. coli.* Wiley InterScience. vol. 17, Issue 6: 1169-1179 (Sep. 5, 2008).

Hertzberg, S., et al. *Mixed photo-cross-linked polyvinyl alcohol and calcium-alginate gels for cell entrapment.* Appl Microbiol Biotechnol, 43: 10-17 (1995).

Premkumar, J.R., et al. *Encapsulation of Luminous Recombinant E. coli in Sol-Gel Silicate Films.* Advanced Materials. vol. 13, No. 23 (Dec. 3, 2001).

Little, B.E., et al. *Ultra-Compact Si-$SiO_2$ Microring Resonator Optical Channel Dropping Filters.* IEEE Photonics Technology Letters, vol. 10, No. 4 (Apr. 1998).

Chin, M.K., et al. *GaAs Microcavity Channel-Dropping Filter Based on a Race-Track Resonator.* IEEE Photonics Technology Letters, vol. 11, No. 12 (Dec. 1999).

Davidov, Y., et al. *Improved bacterial SOS promoter:: lux fusions for genotoxicity detection.* Mutation Research 466 97-107 (2000).

Sagi, E., et al. *Fluorescence and bioluminescence reporter functions in genetically modified bacterial sensor strains.* Sensors and Actuators B 90 2-8 (2003).

Biran, I., et al. *Optical Imaging Fiber-Based Single Live Cell Arrays: A High-Density Cell Assay Platform.* Anal. Chem. 74, 3046-3054 (2002).

Biran, I., et al. *Optical imaging fiber-based live bacterial cell array biosensor.* Analytical Biochemistry 315 106-113 (2003).

Kip, D. *Photorefractive waveguides in oxide crystals: fabrication, properties and applications.* Applied Physics B 67, 131-150 (1998).

\* cited by examiner

CONCURRENT MONITORING OF A PLURALITY OF SAMPLES BY AN ARRAY OF BIOSENSING ELEMENTS

FIELD OF THE INVENTION

This invention is generally in the field of sensing techniques, and relates to a system and method for concurrent monitoring of a plurality of samples by an array of biosensing elements while in contact with the samples.

REFERENCES

The following references are considered to be pertinent for the purpose of understanding the background of the present invention:
1. Belkin, S, 2003. Whole-cell environmental sensing of pollutants. Current Opinion Microbiol., 6: 206-212.
2. Daunert, S., Barrett, G, Feliciano, J. S., Shetty, R. S., Shrestha, S. and Smith-Spencer W. 2000. Genetically engineered whole-cell sensing systems: coupling biological recognition with reporter genes. Chem. Rev. 100: 2705-2738.
3. Kohler, S., S. Belkin and R. D. Schmid. 2000. Reporter gene bioassays in environmental analysis (review). Fresen. J. Anal. Chem. 366: 769-779
4. Walmsley, R. M., N. Billinton and W. D. Heyer, 1997. Green fluorescent protein as a reporter for the DNA damage-induced gene RAD54 in *Saccharomyces cerevisiae*, Yeast 13
5. Van Dyk T K, DeRose E J, Gonye G E. 2001. LuxArray, a high-density, genomewide transcription analysis of *Escherichia coli* using bioluminescent reporter strains. J. Bacteriol. 183: 5496-505.
6. R. Hofmeister, S. Yagi, A. Yariv, and A. J. Agranat, "Growth and Characterization of KLTN:Cu, V Photorefractive Crystals", J. Cryst. Growth 131, pp 486-494 (1993).
7. M. Sasaura, K. Fujiura, K. Enbutsu, T. Imai, S. Yagi, T. Kurihara, M. Abe, S. Toyoda, and E. Kubota, US Patent Application 0072550 (2003).
8. A. J. Agranat, R. Hofmeister and A. Yariv, "Characterization of a New Photorefractive Material: K1-y LiyTal-x NbxO3", Optics Letters 17, 713 (1992).
9. A Gumennik, "Waveguide construction by high Energy Alpha Particles implantation". MSc thesis in Applied Physics, The Hebrew University of Jerusalem (2005).
10. D. Kip "Photorefractive waveguides in oxide crystals: fabrication, properties, and applications" Appl. Phys. B 67, 131-150 (1998).
11. Polyak, B., E. Bassis, A. Novodvorets, S. Belkin and R. S. Marks. 2001. Bioluminescent whole cell optical fiber sensor to genotoxicants: system optimization. Sensors & Actuators B 74: 18-26.
12. Köhler, S., T. T. Bachmann, J. Schmitt, S. Belkin and R. D. Schmid. 2000. Detection of 4-chlorobenzoate using immobilized recombinant *Escherichia coli* reporter strains. Sensors & Actuators B 70: 139-144.
13. Lyngberg O. K, Ng C P, Thiagarajan V, Scriven L E, Flickinger M C. 2001. Engineering the microstructure and permeability of thin multilayer latex biocatalytic coatings containing *E. coli*. Biotechnol Prog. 17:1169-1179.
14. Hertzberg, S., E. Moen, C. Vogelsang and K. Østgaard. 1995. Mixed photo-cross-linked polyvinyl alcohol and calcium alginate gels for cell entrapment. Appl. Microbiol. Biotechnol. 43: 10-17.
15. Rajan Premkumar, J., O. Lev, R. Rosen and S. Belkin, 2001. Encapsulation of luminous recombinant *E. coli* in sol-gel silicate films. Adv. Materials 13: 1773-1775
16. B. E. Little, et al., "Ultra-compact Si—SiO2 microring resonator optical channel dropping filters," IEEE Photonics Technology Letters 10, 549-551 (1998).
17. M. K. Chin, et al., "GaAs microcavity channel-dropping filter based on a race-track resonator," IEEE Photonics Technology Letters 11, 1620-1622 (1999).

BACKGROUND OF THE INVENTION

Biosensors are devices that identify chemical or biological entities with high selectivity on the basis of molecular recognition. Biosensor devices integrate the assay substrate and sensor element into a single device.

The advantage of most bio-sensing devices lies in the extremely high specificity of interactions of biological molecules. Thus, biosensors have been based on the specific interactions between enzymes and their substrates, the recognition between antibodies and antigens, accessibility of specific target molecules (ligands) to their receptors, or the high affinity of nucleic acids strands to their complementary sequences. In all of these, the focus is on the specificity endowed by the unique recognition of two molecules.

A completely different analytical approach is allowed when the biological entity in question is not a molecule but rather a live, intact cell [1, 2, and 3]. The intact, living microbial cells have been genetically engineered to produce a measurable signal in response to a specific chemical agent or physical change in their environment. This triggers very complex series of reactions that can exist only in an intact, functioning cell. Thus, global parameters such as toxicity or genotoxicity can be assayed by using whole cells. Molecular recognition or chemical analysis can rarely provide this type of information. Among whole-cell biosensors, the most promising ones to date are those based on single cell organisms such as bacteria or yeast [2, 4, and 5].

Microbial biosensors are based on the ability of microorganisms to continuously monitor their microenvironment and respond to local environmental changes by expressing specific expression products. In recent years genetic engineering methods have been developed to create types of bacteria that respond to minute quantities of specific chemical or biological substances. The response of the bacteria may be manifested in different ways which include the generation of either luminescent or florescent molecules, or by the production of a minute electrical charge (for example due to production of ionic channels). This response can be detected by a sensitive measurement system that generates an electronic signal the analysis of which yields an indication of the presence of the pursued substance.

As illustrated in FIG. 1, biosensing microorganisms contain two essential genetic elements, a transcription regulatory element (promoter and/or enhancer sequence) and a reporter gene coding for an expressible product. The promoter element is turned on when the target agent is present in the cell's environment. Turning on the promoter causes the reporter gene to be transcribed. Activation of the reporter gene leads to production of reporter proteins that generate some type of a detectable signal either directly (by florescence or luminescence) or by working enzymatically on substrates. Therefore, the presence of a signal indicates that the biosensor has sensed a particular target agent in its environment. For several types of biosensors using for example Green fluorescent protein (GFP) as exemplified in FIG. 1, or Uroporphyrinogen (Urogen) III Methyltransferase (UMT) as reporter gene, the signal must be activated by an external light source.

GENERAL DESCRIPTION

There is a need in the art in facilitating concurrent monitoring of a plurality of samples, by an array of biosensing elements (e.g. microbial sensing elements) arranged in a spaced-apart relationship, where the detection of the response of the biosensing element is carried out by excitation of the latter while in contact with the sample by a certain stimulus, and detecting the sensing element response to this excitation.

The term "concurrent" used herein signifies substantial simultaneous excitation of the multiple biosensing elements, and substantial simultaneous collection of response signals therefrom.

The term "monitoring" refers to identifying the specific biosensing element by its location in an array of spaced-apart biosensing elements, thereby enabling to identify the respective sample and/or target agent. Where the array of biosensing elements is intended to be used in a plurality of different tests on the same sample (blood from one individual), location or measurement site X1Y1 holds a biosensing element (e.g. a population of sensing microorganisms) responsive to one target molecule, location X2Y2 holds a different population responsive to another target molecule, etc., so that a single array may identify the different target agents by the site that responded to exciting field. Where the array of biosensing elements is intended to be used in the same tests (for example identification of drug Z) on different samples (blood obtained from several individuals), all locations may have the same population of biosensing elements and the single array may test for the same target agent from several individuals, and in this case the specific location (site) in the array identifies the individual.

The term "sample" in the context of the invention refers to a specimen (typically liquid, but may be a solid or gaseous specimen, placed in a liquid medium) suspected of having one or more target molecules. By one option the same sample (for example blood obtained from a single individual) is distributed among the sites of the array so that multiple tests for the presence of different target molecules in the sample may take place. By another option different samples (for example blood obtained from several individuals) are placed in the different locations for detection of the same of different target molecules. Both these options are referred to in the text as "samples".

The term "target agent" refers in the context of the present invention to a chemical or biological molecule, to a complex of molecules, or to an identifiable part of such a molecule or complex that needs to be detected. This may be done for diagnosis purposes (detection of a biological agent, drug, toxin in a body (liquid) sample), for industrial purposes, (detection of a product or contaminant in a sample), for homeland security purpose (detection of a harmful biological or chemical agent etc.), or for environmental purposes. It should be noted that the biosensing elements may respond to the target agents in a yes/no binary fashion, but it is also possible to create populations of microbial elements that start to respond at different levels of the target agents and by this also identify the amount/level of the target agent.

The present invention provides a novel monitoring device and method, as well as a novel method of the device fabrication utilizing a KLTN-based material.

The main idea of the monitoring technique of the present invention consists of concurrent excitation of the multiple biosensing elements, arranged in spaced-apart relationship in an array of sites, by an array of exciting signals with different excitation parameters, respectively, for example an array of pulsed signals with different pulsing frequencies. This allows for using a single detection element for detection of response signal coming from the array of biosensing elements, and identifying in the collected response signal a location of the biosensing element responding by a signal part tagged by the different parameters (e.g. pulsing frequency) of excitation.

As each location of the array is excited by a unique pulsing frequency (different from that of the other locations), it is possible to identify in the combined signal from a plurality of locations, which pulsing frequency of the emitted light contributed to the combined signal, and by this to identify the site of the array that responded. As each site is designed to hold a biosensing element responsive to a specific target molecule, this allows for identification of one or more molecules in the sample.

More specifically, the present invention is used for optical monitoring of biosensing elements (e.g. microbial sensing elements) which produce a detectable signal in the presence of target agent(s), namely monitoring using excitation that causes optical response of the biosensing element while in contact with a sample. One advantage of the present invention is the ability to use a photomultiplier detector, thus increasing the sensitivity of detection, as compared to the active matrix pixel based detectors, such as CCD. Another important advantage of the present invention is the ability to use of a single stationary mounted photomultiplier for concurrent signal detection from multiple biosensing elements, thus eliminating a need for scanning the sensing element array for element-by-element detection, or eliminating the expensive and cumbersome use of a plurality (array) of photomultipliers.

According to one broad aspect of the present invention, there is provided a system for monitoring detectable responses from multiple biosensing elements while in contact with multiple samples located in an array of spaced-apart sites, the system comprising:

an exciting unit configured and operable for producing an array of exciting signals each characterized by a frequency differing from that of the other exciting signals, and exciting a corresponding array of the biosensing elements by said array of signals, respectively, so that each biosensing element of said array is excited by a different exciting signal, thereby enabling each biosensing element to generate a response signal tagged by said different frequency; and a detection unit comprising a single receiving element associated with said array of biosensing elements and configured for concurrently receiving the multiple response signals and generating a single output signal indicative thereof;

The system thereby enabling to identify, in said single output signal, signal parts corresponding to the response signals of the spatially separated biosensing elements, based on the different frequencies in the response signals coming from the different sites.

In preferred embodiments of the invention, the exciting signals are pulsed signals, and different tagging frequencies are pulsing frequencies of the exciting pulses.

According to another broad aspect of the present invention, there is provided a system for monitoring detectable responses from multiple biosensing elements while in contact with multiple samples located in an array of spaced-apart sites, the system comprising:

an exciting unit configured and operable for producing an array of exciting signals, each being a pulsed signal having a pulsing frequency differing from that of the other exciting signals, and exciting a corresponding array of the biosensing elements by said array of signals, respectively, so that each biosensing element of said array is excited by a predefined pulsing frequency different from that of the other sensing elements, thereby enabling each biosensing element to generate a response signal of a different pulsing frequency; and a detection unit comprising a single receiving element associated with said array of biosensing elements and configured for concurrently receiving the multiple response signals and generating a single output signal indicative thereof;

The system thereby enabling to identify, in said single output signal, signal parts corresponding to the response signals of the spatially separated biosensing elements, based on the different pulsing frequencies of the response signals coming from the different sites.

The system is associated with a data processing unit, which may be a constructional part of the system or may be connectable thereto (via wires or wireless signal transmission). The data processing unit includes appropriate software and/or hardware utility configured and operable for processing the output signal generated by the detector, by separating this output signal into its Fourier components. By this, signal parts coining from different locations are identified, thereby enabling to identify the location of the responding biosensing element and hence to identify the target agent in the sample to which the specific biosensing element responded to. The data processing unit may also include a phase locking utility configured and operable for identifying different phases for the Fourier components respectively, and thereby improving the detectivity of the response.

In some embodiments of the invention, the exciting unit is an optical unit producing the exciting light beams of different pulsing frequencies. Generally, the exciting unit may be of kind capable of generating an appropriate stimulus such as an acoustic wave, an electric field, etc., in the form pulses of different pulsing frequencies, by which an optical modulator such as an electrooptical modulator, a micro electromechanical modulator, or an acousto-optic modulator can be controlled.

In some embodiments of the invention, the receiving (detecting) element is a photomultiplier detector receiving the optical response signals and generating the single electrical output signal.

The exciting unit may be configured to excite the biosensing elements with light capable of exciting a signal emitting molecule which is produced in at least one of the biosensing elements while in contact with a sample. The exciting light may be configured to generate light capable of causing single- or multi-photon interaction with the signal emitting molecule (e.g. electroluminescence or florescence emitting molecule) that is generated in response to the presence of the target element in at least one of the biosensing elements.

In an embodiment of the invention, the optical exciting unit includes a light distributor for distributing light of an exciting wavelength range in the form of the array of light beams towards the spaced-apart sites; and an array of optical modulators (e.g. electrooptic modulators, acousto-optic modulators or MEMS based modulators). The optical modulators are accommodated in optical paths of the light beams propagating towards the array of spaced-apart sites and are configured and operable to modulate the light beams with the different pulsing frequencies. The light distributor may include a power distributor for receiving light from a light emitter and producing a plurality of light components of substantially the same power, and an optical power grid adapted to controllably direct the exciting light to said plurality of sites. The optical power grid may be configured as an arrangement of light guiding elements, interconnecting the power distributor and said sites.

In an embodiment of the invention, the exciting unit is implemented within a substrate, which is formed with the spaced-apart sites for carrying the biosensing elements, while a light emitter is external to the substrate. The substrate is preferably a KLTN-based material.

The power grid may include a network of waveguides interconnected by optical switching devices. The waveguides are preferably operative in a visible spectrum. The optical power grid may further include a plurality of optical switches located at the network junctions and configured for performing selective distribution of the exciting light propagating through the waveguides to said sites. The optical switches may include a ring cavity waveguide (RCW), or a digital optical switch.

According to another aspect of the invention, there is provided an electro-optic system for use in identifying detectable responses from a plurality of biosensing elements located in contact with a plurality of samples in spaced-apart sites, respectively, the system comprising:

an electro-optic structure having an array of spaced-apart sites intended for containing a corresponding array of biosensing elements, and being configured for producing optical signals of different pulsing frequencies at said sites, respectively; and, at least one single-photomultiplier based unit adapted to detect in parallel multiple light signals of different pulsing frequencies coining from different sites, generate a single electrical output indicative thereof, and process said output to identify the site location corresponding to the pulsing frequency, thereby enabling to identify the biosensing elements generating the response.

In some embodiments of the invention, the electro-optic system is configured to produce optical signals capable of exciting the biosensing elements to cause generation of the optical response of a target agent (e.g. fluorescent molecule) created in the biosensing element as a result of its interaction with the sample.

By one option the plurality of biosensing elements identifies the same target agents in a plurality of different samples. By another embodiment the plurality of biosensing elements identifies different target agents in a single sample divided between the sites. By yet another embodiment the plurality of biosensing elements identifies a plurality of different target agents in a plurality of different samples.

According to yet another aspect of the invention, there is provided a method for monitoring multiple samples and/or multiple target agents by monitoring detectable responses generated by a plurality of biosensing elements while in contact with a plurality of samples, respectively, located in an array of spaced-apart sites, the method comprising:

exciting an array of the biosensing elements by an array of exciting signals, each being a pulsed signal having a pulsing frequency differing from that of the other exciting signals, so that each biosensing element of said array is excited by a predefined pulsing frequency different from that of the other biosensing elements, thereby enabling each biosensing element to generate a response signal of a different pulsing frequency;

concurrently receiving the response signals by a single receiving element and generating a single output signal indicative of the received signals; and processing said single output signal based on the different pulsing frequencies of the response signals coming from the different biosensing elements, for identifying in said single output, signal parts corresponding to the response signals coming from the spaced-apart sites, thereby enabling identification of the existence and location of at least one sample and/or target agent.

The biosensing elements in the multiple site may be identical to each other (when monitoring the same molecules in a plurality of different sample specimens) or may be different in different sites by their selectivity to the target agent or selectivity to the level of the target agent, i.e. each biosensing element creates the detectable label in response to a specific and different target agent (or a different level of the target agent). The detectable label created may be the same or different in each biosensing element, as the identification is not based on the nature of the detectable label (all can be the same florescent protein) but on the site location in the array (the site associated with a unique pulsing frequency).

The biosensing array may be a whole-cell array referring to the concept in which the array format is composed of intact, live, microbial cells. The biosensing element may comprise whole cells selected from bacteria, yeast and protozoa.

According to yet further aspect of the invention, there is provided a method of fabricating an electro-optical circuit within a KLTN-based material for use in monitoring multiple biosensing elements (e.g. microbial sensing elements) located in respective sites in said structure, the method comprising:

a. bombarding said KLTN-based material with high energy ions to create a cladding layer of partially amorphous material, while controlling the depth of said layer by controlling the energy of said implanted ions and controlling the thickness of said layer high energy ions by controlling the dosage of said implanted ions; and, b. creating in the KLTN crystal a waveguiding layer sandwiched between the crystal surface and the said cladding layer, c. creating at least one optical switching device and at least one electro-optic modulator in said waveguiding layer of KLTN crystal sandwiched between the said cladding layer and the crystal surface, by selective spatial implantation of light ions (e.g. $H^+$, $He^+$ carbon ions or oxygen ions) at a predetermined high energy.

The expression "selective spatial implantation" refers to the lateral distribution of the ions bombardment.

Thus, the present invention provides an electro-optic structure for biosensing elements that includes spatial and temporal (the latter term referring to different pulsing frequencies) selectivity of the target agents so that a single sensitive detector element can be used without sacrificing the variance of monitored substances inherent to the array concept.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
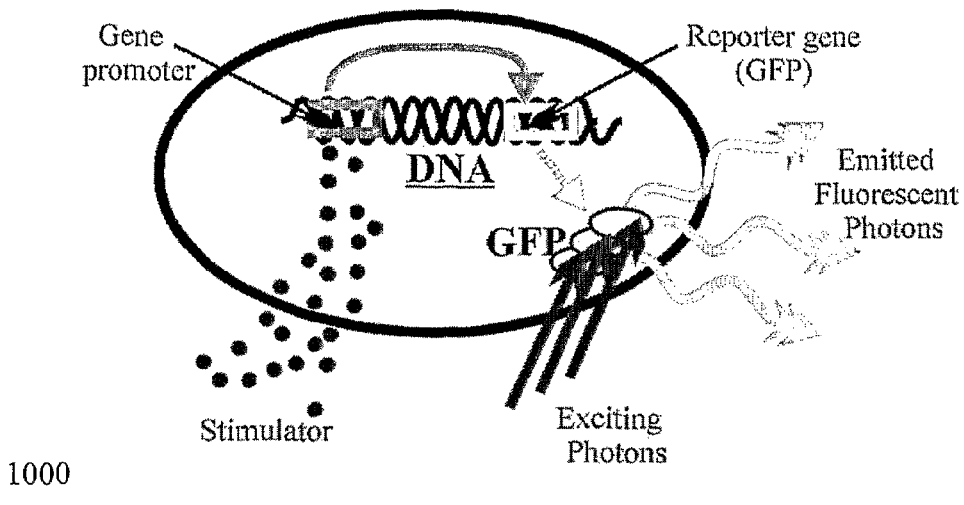
FIG. 1 is a schematic illustration of the principles of the known technique for fluorescent sensing in a microbial sensing cell.

FIG. 1 illustrates general principles of identifying a sample by its interaction with a microbial biosensing element, that might result in the production of a fluorescent molecule signifying the presence of the target element. Applying exciting light to the biosensor allows for detecting the fluorescence if any, and thus identifying the sample and/or the target agent.

The present invention takes advantages of the above technique, and provides a novel method and system enabling concurrent monitoring of multiple samples while interacting with multiple biosensing elements.

More specifically, the present invention utilizes optical monitoring technique applied to biosensing elements of the kind responding by fluorescence, when a fluorescent molecule is created as a result of the biosensing element interaction with a sample, and is therefore described below with respect to this specific application. It should however be noted that the invention is not limited to this specific example, and the excitation may be of a different type, as well the response signal may also be of a different type, e.g. a change in electrical properties of the sample. It should also be noted that a detectable response of the biosensing element (e.g. fluorescence) may be caused by one- or multi-photon excitation.

Figure 2:
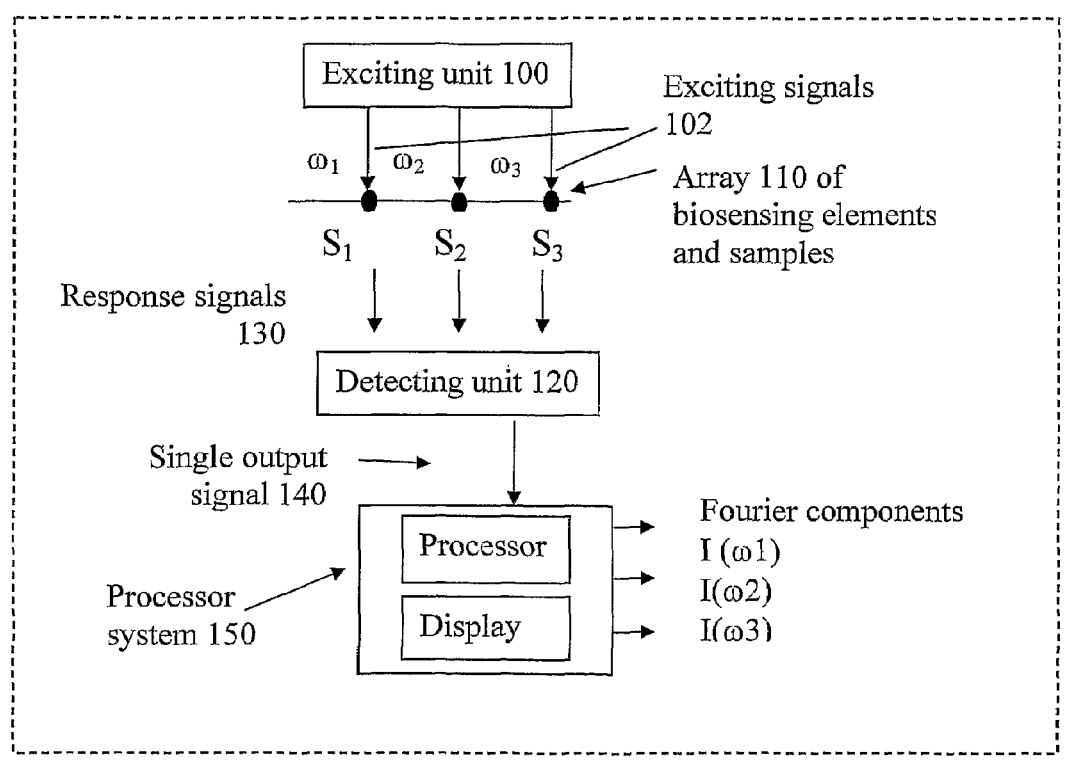
FIG. 2 is a schematic block diagram of a monitoring system according to one embodiment of the present invention.

Reference is made to FIG. 2, presenting a block diagram of the system of the present invention. The system 1000 is useful for concurrent monitoring of a plurality of samples while in contact with a plurality of biosensing elements located in an array of spaced-apart sites. The different biosensing elements may be used for different tests on the same sample, the similar biosensing elements may be used for the same tests on different samples at different sites.

System 1000 comprises an exciting unit 100 configured and operable for producing an array of exciting signals 102 for exciting a corresponding array of the biosensing elements 110 by said array of signals 102, respectively. Each exciting signal 102 is characterized by a frequency different from that of the other signals. In some embodiments of the invention, the exciting signal is a pulsed signal having a pulsing frequency differing from that of the other exciting signals. Three such exciting signals of different pulsing frequencies $\omega_1$, $\omega_3$, $\omega_3$ associated with three sites $S_1$-$S_3$ (biosensing elements) respectively being shown in the present example. Hence, each biosensing element of said array 110 is excited by a predefined pulsing frequency different from that of the other biosensing elements, thereby enabling each biosensing element to generate a response signal "tagged" by a different pulsing frequency of excitation, in the simplest example—response signal with the corresponding pulsing frequency of the excitation.

System 1000 also includes a detection unit 120 comprising a single (stationary mounted) receiving element associated with said array of biosensing elements 110 and configured for concurrently receiving signals 130 coming from the biosensing elements and generating a single output signal 140 indicative thereof. System 1000 thereby enables to identify, in said single output signal 140, signal parts corresponding to the response signals of the spatially separated biosensing elements 110, based on the different pulsing frequencies of the response signals coining from the different sites and being thus generated by different biosensing elements 110.

A data processing system 150 is provided being connectable (via wires or wireless) to the output of the detection unit 120 and including a data processor and a data presentation utility (e.g. display). The data processing system 150 includes appropriate software and/or hardware utility is configured and operable for processing the output signal 140 by separating said output signal into its Fourier components, and obtaining the signal parts coining from different locations. By this, the location of the responding biosensing element 110 can be identified. Data processor 150 may also include a phase locking utility for identifying the different phases of the Fourier components, thereby improving the detectivity of the response and thus increasing the signal to noise ratio and simplifying identification of the sample and/or target agent. It should be understood that the system of the present invention is not limited to any specific number of identifiable samples, and/or any number of biosensing elements.

According to one embodiment of the present invention, in one specific example, exciting unit 100 is an optical unit producing an array of light beams of the different pulsing frequencies ($\omega 1, \omega 2, \omega 3 \ldots$). The response signals generated by one or more biosensing element are optical signals, e.g. signal generated by fluorescent molecules. The optical signals are then imaged onto a single stationary mounted receiving element 120 such as a photomultiplier adapted to generate a single electrical output signal.

Figure 3A:
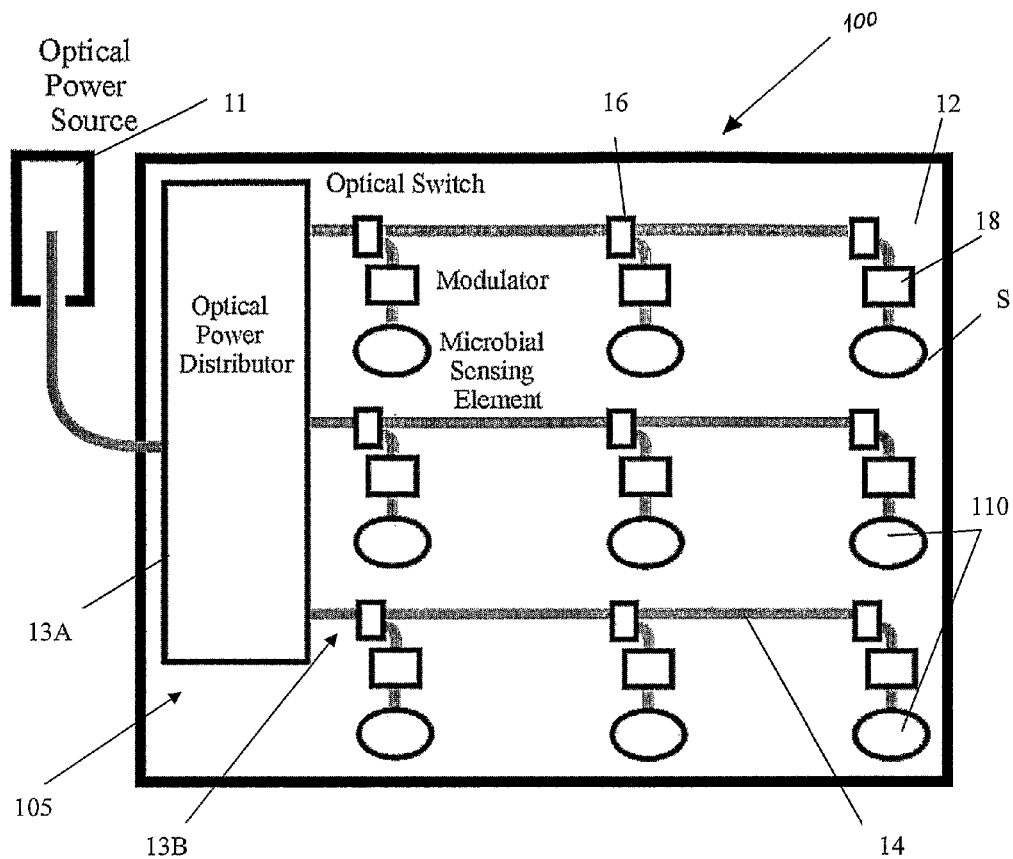
FIG. 3A exemplifies an exciting unit according to the invention to be used in the system of FIG. 2.

Referring to FIG. 3A, there is shown an example of an exciting unit 100 operative to detect the presence of a plurality of chemical or biological species. Here, the exciting unit 100 is incorporated with a samples' carrier, including a substrate 12, a KLTN substrate in the present example, carrying an array of spaced-apart sites, generally at S, configured for containing an array of biosensing elements, generally at 110, each in contact with a sample.

Potassium lithium tantalate niobate (KLTN) crystal is an oxygen perovskite that was co-invented by the inventor of the present application. KLTN is an electro-optic crystal having a formula $K_{1-y}Li_yTa_{1-x}Nb_xO_3$, wherein x is between 0 and 1 and y is between 0.0001 and 0.15. Bulk KLTN crystals can be grown for example by the top seeding solution growth method [6], by the liquid phase epitaxial growth on top of a KLTN bulk substrate, or by the metal-organic chemical vapor deposition (MOCVD) technique on silicon or silicon oxide, as well as Alumina and magnesium oxide substrates [7]. The resulting films maintain all the physical characteristics of bulk materials, while improving the uniformity of composition.

In the field of oxygen perovskites ferroelectric crystals, it is known that the phase transition temperature $T_c$ of such crystal is strongly affected by the presence of impurities and defects. For example, the replacement of a Ta ion in potassium tantalate niobate (KTN) by an Nb ion will cause a change in $T_c$ of magnitude: $\Delta T_c \approx 7.0/1\%$ per mole of Nb. A similar effect can be achieved by replacing a K ion in KTN by either Li or Na. Here the effect is more dramatic and results in certain cases in $\Delta T_c \approx 50$ K/1% per mole of Li [8].

KLTN demonstrates a very strong quadratic electro-optic effect at the paraelectric phase [8]. This effect is given by $\Delta n = -(1/2)n_o^3 g_{eff} P^2$, where $\Delta n$ is the induced change in the index of refraction, $n_o$ is the index of refraction, $g_{eff}$ is the effective (quadratic) electro-optic coefficient, and P is the static (or low frequency) electric polarization induced by the applied field E. At the paraelectric phase the polarization P is given by $P = \epsilon_o(\epsilon_r - 1)E \approx \epsilon E$, where $\epsilon_o$ is the electric permeability, and $\epsilon_r$ is the relative dielectric constant. Typically $n_o = 2.25$ and $g_{eff} = 0.2$ $C^2/m^4$ for KLTN.

The electro-optic effect is driven by the induced polarization. In most cases, lithium niobate and other conventional electro-optic crystals are typically used in a phase where they manifest large spontaneous polarization, e.g. well within the ferroelectric phase. Therefore not much polarization is left to be induced, i.e. the polarization is close to saturation. In KLTN at the paraelectric phase there is no spontaneous polarization so that the external electric field can induce a very large polarization change.

In the case of KLTN, a working temperature of an electro-optical device utilizing the quadratic electro-optic effect can be slightly above the phase transition temperature (it was found that at such temperatures KLTN maintains high optical quality and fast dielectric response time). In KLTN the relative permeability of $\epsilon_r = 2 \cdot 10^4$ can for example be provided. If an electric field $E = 3 \cdot 10^3$ V/cm is then applied to the KLTN crystal, the induced birefringence will be $\Delta n = 6 \cdot 10^{-3}$. This is roughly two orders of magnitude higher than the induced birefringence obtained in other electro-optic materials, such as $LiNbO_3$. KLTN crystal was found to be a chemically inert, non-hygroscopic and stable material, so that it is not expected to manifest gradual deterioration in performance.

Turning back to FIG. 3A, exciting unit 100 includes an exciting energy distributor 105, light distributor in the present example (which includes a power distribution module 13A and an optical power grid 13B), adapted to controllably distribute light of an exciting wavelength range in the form of a light beams array towards the predetermined spatially separated sites S. The light distributor receives light from an optical power source 11 (e.g. light emitter such as a laser source), which may or may not be mounted on the substrate 12 (external optical power source being used in the present example). The optical power source 11 is adapted to provide light of the wavelength range capable of exciting target molecules.

As described herein, the biosensing elements comprise a selectivity component capable of selectively interacting with a target agent and a reporter entity that produces a detectable signal upon interaction of the selectivity component with a target agent. The selectivity component may be a polypeptide (including antibodies or antigens, receptor or ligands, substrates or enzymes, DNA binding molecules that bind DNA aptamers, and fragments and variants thereof), polynucleotides (including aptamers) that can bind to complementary sequences, glycosilated molecules that bind to leptons, template imprinted materials, and organic and inorganic binding elements. The reporter entity, that produces a detectable signal, is typically an expression product that is expresses, upon affinity binding of the selectivity component to the target agent, or an entity that is altered (for example upon enzymatic activity) upon said binding. The reporter entity may also be sensitive to changes in the environment, including, for example, pH sensitive molecules, polarity sensitive molecules, restriction sensitive molecules, or mobility sensitive molecules. A specific example of a selectivity component is an expression regulatory element such as a promoter, that upon binding of the target agent, initiate the production of a protein that can be detected (such as a florescent protein).

The system of the present invention is adapted to environmental applications e.g. the detection of pesticides and river water contaminants; the detection of pathogens or the determination of the levels of toxic substances.

Biosensing element 110 exists in different forms based on a variety of storage and immobilization techniques such as droplets, beads, sol-gel glass. In an exemplary embodiment, the detection is based on the fluorescence scheme in which the biosensing elements activate a sequence resulting with the generation of a fluorescent molecule such as Green Fluorescent Protein. The biosensing element (e.g. the sensing microbes) is incorporated into the device in a manner that allows contact with the sample, measurement of the developed signal, its amplification and its translation into usable units. Past reports have described partial successes using immobilization procedures based on matrices such as alginate [11], agar [12], latex [13], polyvinyl alcohol [14] or sol-gel [15]. The principles of interaction between a biosensing element and a sample resulting in the creation of a target molecule (typically fluorescent molecule) responding to exciting light, are known per se and therefore need not be described in details.

In the present example, the light distributor 105 includes a power distribution module 13A and an optical power grid 13B. The latter is constructed of a plurality of waveguiding light conduits 14 interconnected by optical switches 16. The light distributor thus directs the exciting light generated by the optical power source 11 to the network waveguiding light conduits 14, which convey the respective light beams towards the spaced-apart sites.

The circuit of waveguides 14 is operative in the visible region of the spectrum. Waveguide 14 is implemented in KLTN substrate 12 operating in the paraelectric phase. One of the advantages of the KLTN-based material is the operation in the visible spectrum at high intensity without developing optical damage. Another advantage lies in the method of constructing high quality stable waveguiding structures by the implementation of high energy ions (larger than 1 MeV) in KLTN-based material. As disclosed in WO 2006/106524 to the same assignee, which publication is incorporated herein by reference, the inventor of the present invention has developed a method for constructing permanent waveguiding structures in the KLTN crystals [9]. The method is based on the creation of amorphous nanostructures in the crystals by the implantation of high energy ions. It is a well established fact that the bombardment of crystals of oxygen perovskites by light ions such as H+ and He+ at energies of several MeVs creates a well defined layer of amorphous material within the crystal [10]. The amorphous material has high optical quality, and its index of refraction is typically 5% to 10% lower than that of the crystal in which it is formed. The depth of the generated layer is determined by the initial energy of the implanted ions, and the thickness of the layer is determined by the dosage of the implantation. KLTN substrate 12 material may be a KLTN crystal. The amorphous KLTN-based material may be formed by an amorphization of the KLTN-based material. Preferably, the configuration is such that the at least one amorphous region contains a significant amount of Frenkel defects. The amorphous region is formed by bombarding of KLTN-based material with light ions. The bombarding ions may include at least one of the following types: H+, D+, He+, Carbon or Oxygen; and may include ions having kinetic energy larger than 1 MeV. The amorphous region of the amorphous KLTN material can be buried inside the KLTN-based material. The region of the amorphous KLTN-based material defines waveguide 14 in KLTN-based material at either side of the amorphous region. Waveguide 14 may be arranged to substantially confine light in one dimension or in two dimensions; as well as may be arranged to allow propagation of light of a single mode.

Turning back to FIG. 3A, the optical power grid 13B distributes light to biosensing elements containing sites S, using different optical switching devices 16 (e.g. digital optical switches) adapted to perform selective distribution of the optical power to the different sites.

Also provided in the exciting unit 100 is an array of modulators 18 which are accommodated in the optical paths of the light beams propagating towards the sites. Each such modulator 18 is adapted to modulate the light passing therethrough with a certain pulsing frequency, different from that of the others. The modulator 18 may be of any suitable type, for example electrooptical, acoustooptical, or MEMS-based modulator.

According to some other embodiments of the invention, the light distributor may include an array of directly driven diode lasers associated with an array of sites containing the biosensing elements mid samples.

Figure 3B:
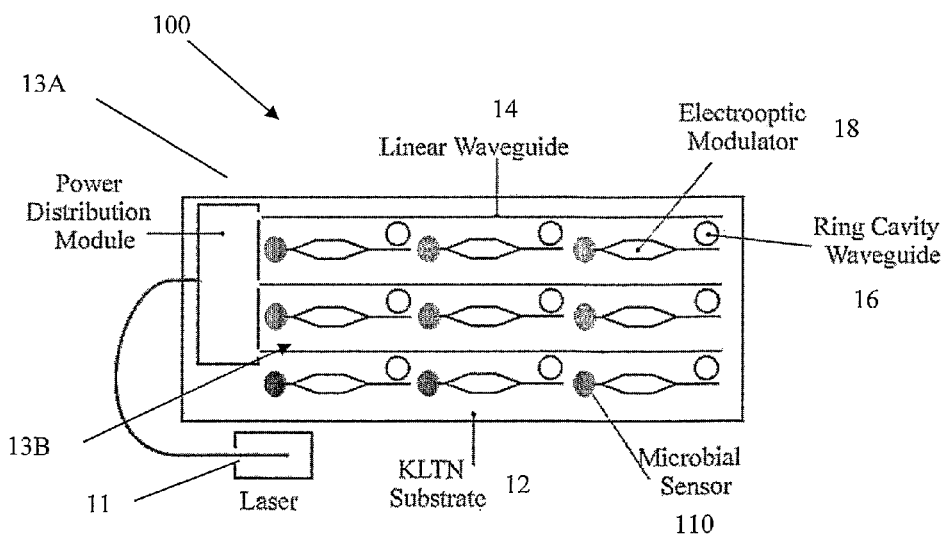
FIG. 3B shows another example of an exciting unit suitable to be used in the system of FIG. 2.

FIG. 3B illustrates a more specific but not limiting example of the configuration of the exciting unit 100. This configuration is generally similar to that of FIG. 3A, but utilizing electro-optical modulators 18 configured as electrooptical Mach-Zender interferometer implemented in a waveguided configuration (e.g. by bombardment of high energy ions into a KTLN substrate 12), optical switching devices 16 in the form of ring cavity waveguides (RCWs) [16,17]. RCW 16 is operative as a valve of the optical power grid, and enables the control of the flow of the exciting light to the location of the respective biosensing element 110. Such RCWs may also be implemented by bombardment of high energy ions in the KTLN substrate 12.

Figure 4:
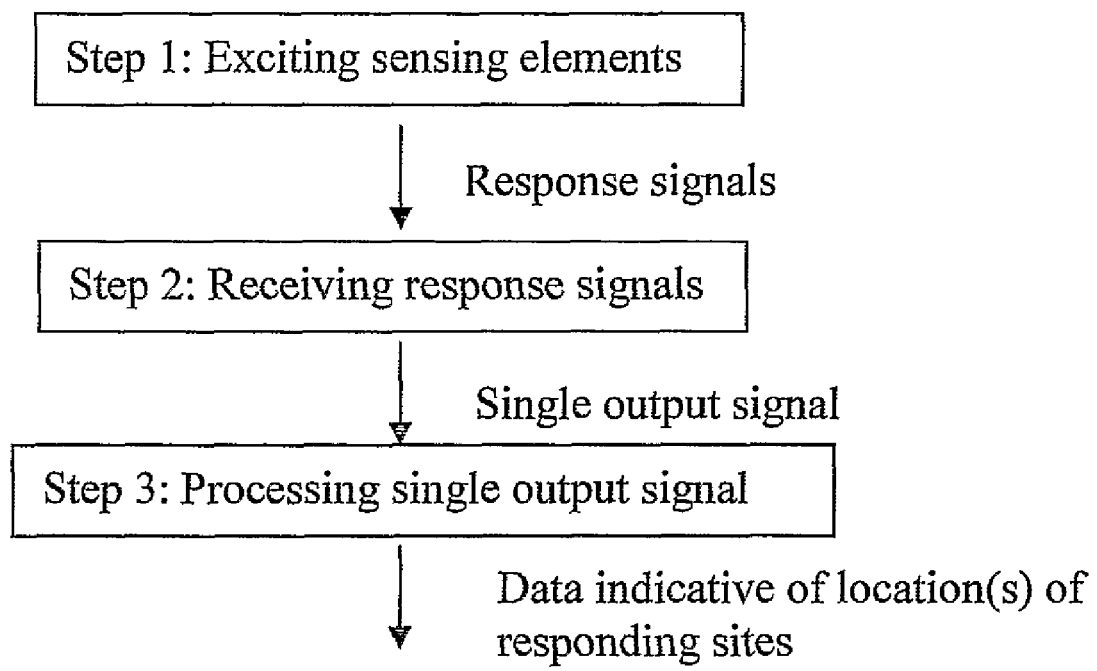
FIG. 4 is a flow chart of an example of a method according to the invention for monitoring multiple samples contained in an array of microbial sensors.

Reference is made to FIG. 4, illustrating a flow chart of an example of a method according to the invention for monitoring multiple samples being in contact with multiple biosensing elements located in spaced-apart sites.

Initially, an array of biosensing elements is provided, where the biosensing elements are arranged at a plurality of pre-defined spaced-apart sites. Each site holds a biosensing element capable of responding to a specific target agent, in the presence of the excitation light, by emitting a detectable optical signal (e.g. fluorescence).

Multiple biosensing elements are concurrently excited (step 1) by an array of exciting signals, where each exciting signal is a pulsed signal having a pulsing frequency differing from that of the other exciting signals. Accordingly, each biosensing element is excited by a predefined pulsing frequency different from that of the other biosensing elements, thereby enabling each biosensing element to generate a response signal of a different pulsing frequency.

Light emitted by the array of biosensing elements is imaged onto a single stationary mounted photomultiplier detector (step 2) adapted to generate an electrical output signal indicative of the received light.

Data representative of the electrical output of the photomultiplier is processed (Step 3) based on the different pulsing frequencies of the response signals coming from the different sites (i.e. different biosensing elements). The processing includes separating the data indicative of the electrical output into its Fourier components. This allows for identifying, in said single output, signal parts corresponding to the response signals coming from the spaced-apart spatially separated sites, thereby enabling identification of the specific pulse frequency indicative of the location of a biosensing element. As a result, the sample and/or the target agent in the sample can be identified.

Figure 5:
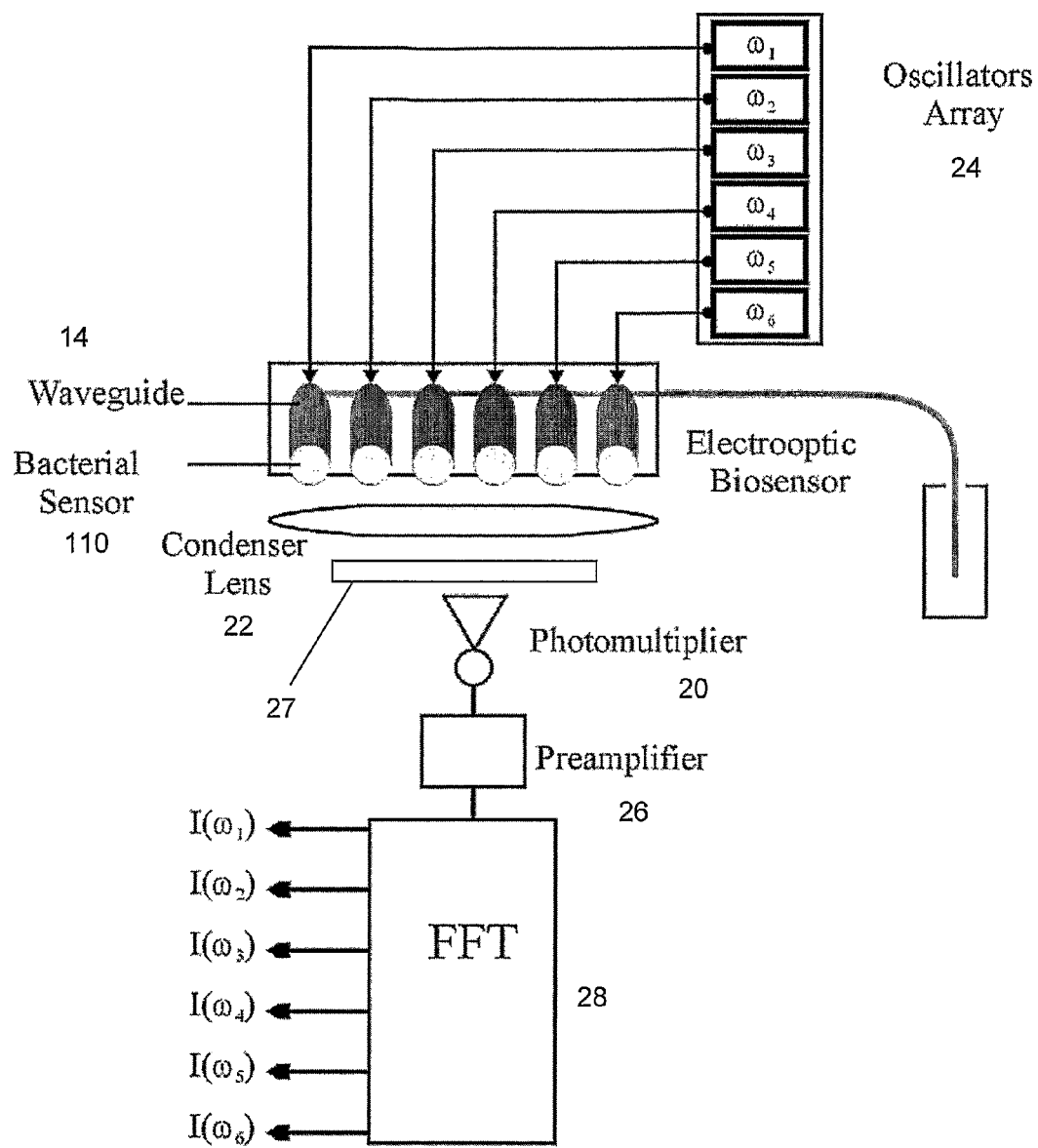
FIG. 5 more specifically illustrates a method of detection using a photomultiplier detector.

Referring to FIG. 5, there is schematically illustrated an example of signal detection using a photomultiplier detector. The photomultiplier is an extremely sensitive detector that maintains its linearity over a very wide dynamic range. However, conventionally, the photomultiplier is a cumbersome device that is not suitable for the construction of imaging arrays. In the method of the present invention, the excitation of each biosensing element 110 (e.g. bacterial cluster) is modulated at a different pulsation frequency. In the present example, this is implemented using a corresponding array of oscillators 24 operating with different frequencies of oscillation. It should be understood that the pulsation frequency is significantly different from the excitation light optical frequency. In a non-limiting example, the entire array (namely the light coming from the entire array) is "imaged" via a condenser lens 22 onto one photomultiplier 20. Preferably, a notch filter 27 (band-stop filter with a narrow stopband or high Q-factor) is provided between the condenser lens and photomultiplier. The single electrical output signal of the photomultiplier 20 passes through a preamplifier 26 to a processor 28. The latter is configured to perform Fast Fourier Transform of the received data, thereby separating the detector's output signal into its Fourier components. Each component is expected to express the signal part produced by its respective biosensing element 110. Optionally, phase locking of each Fourier component to its respective excitation frequency is performed, thereby improving the signal to noise ratio of the detected signal.

The invention claimed is:

1. A system for monitoring detectable responses from multiple biosensing elements while in contact with multiple samples present located in an array of spaced-apart sites, the system comprising:

an exciting unit configured and operable for producing an array of exciting signals each comprising a frequency differing from those of the other exciting signals, and exciting a corresponding array of the biosensing elements by said array of signals, respectively, so that each biosensing element of said array is excited by a different exciting signal, thereby enabling each biosensing element to generate a response signal tagged by the different frequency;

a detection unit comprising a single receiving element associated with said array of biosensing elements and configured for concurrently receiving the multiple response signals and generating a single output signal indicative thereof; and a data processor configured and operable for processing the output signal by separating said signal into its Fourier components, and obtaining the signal parts coming from different locations, thereby enabling to identify the location of the responding biosensing element, the data processor comprising a phase locking utility configured and operable for identifying different phases of the Fourier components, respectively;

the system thereby enabling to identify, in said single output signal, signal parts corresponding to the response signals of the spatially separated biosensing elements, based on the different frequencies in the response signals coming from the different sites.

2. The system of claim 1, wherein each of the exciting signals is a pulse signal having the pulsing frequency differing from those of the other exciting signals.

3. The system of claim 1, characterized by at least one of the following: said exciting unit is an optical unit, said exciting signals being light beams of the different pulsing frequencies; and the response signals are optical signals, the receiving element being a photomultiplier detector concurrently receiving the light signals and generating the single electrical output signal.

4. The system of claim 3, wherein said light distributor comprises a power distributor for receiving light from a light emitter, and an optical power grid adapted to controllably direct the exciting light to said sites.

5. The system of claim 4, wherein the optical power grid has at least one of the following configurations: (i) is configured as an arrangement of light guiding elements, interconnected between the power distributor and said sites; (ii) comprises a network of waveguides interconnected by optical switches.

6. The system of claim 4, wherein the optical power grid comprises a network of waveguides interconnected by optical switches, said waveguides being operative in a visible spectrum.

7. The system of claim 4, wherein said optical power grid comprises a network of waveguides interconnected by optical switches, and a plurality of optical switching devices located at junctions of the power grid network and configured for performing selective distribution of said exciting light propagating through the waveguides to said sites.

8. The system of claim 7, wherein said optical switching devices are selected from a ring cavity waveguide (RCW) and digital optical switch.

9. The system of claim 4, wherein the optical modulators are installed in predetermined locations within said optical power grid, and are operable for performing temporal modulation of said exciting light.

10. The system of claim 9, wherein said optical modulator comprises an electrooptically controlled Mach-Zender interferometer implemented in a waveguided configuration.

11. The system claim 3, wherein the optical exciting unit comprises a light distributor for distributing light of an exciting wavelength range in the form of the array of light beams towards the spaced-apart sites; and an array of modulators which are accommodated in optical paths of said light beams propagating towards said sites and are configured and operable to modulate the light beams with the different pulsing frequencies, the system comprising a substrate formed with said spaced-apart sites for carrying the biosensing elements, said substrate being configured for carrying said light distributor.

12. The system of claim 11, wherein said substrate is configured as an electro-optic structure with the light distributor being integral in said substrate.

13. The system of claim 12, wherein the optical modulators are integral in said substrate.

14. The system of claim 11, wherein the light emitter is located outside said substrate.

15. The system of claim 11, wherein said substrate is a KLTN-based material.

16. The system of claim 1, wherein said exciting unit is an optical unit, said exciting signals being light beams of the different pulsing frequencies, said optical exciting unit having one of the following configurations:

(a) optical exciting unit comprises: a light distributor for distributing light of an exciting wavelength range in the form of the array of light beams towards the spaced-apart sites; and an array of modulators which are accommodated in optical paths of said light beams propagating towards said sites and are configured and operable to modulate the light beams with the different pulsing frequencies;

(b) optical exciting unit comprises: a light distributor for distributing light of an exciting wavelength range in the form of the array of light beams towards the spaced-apart sites, said light distributor comprising an array of diode lasers associated with said array of spaced-apart sites and operable to produce the array of pulsed light beams with the different pulsing frequencies;

(c) the optical exciting unit is associated with a light emitter adapted for generating the exciting light of the wavelength range capable of exciting molecules generated in response to the presence of the target agent in the biosensing elements causing the response light signals therefrom;

(d) the optical exciting unit is configured to activate with light a signal emitting molecule generated by at least one of the biosensing elements while in contact with the sample, resulting in the emission of a response signal.

17. The system of claim 16, wherein the modulator includes at least one of the following light modulators: electrooptical, acoustooptical, and MEMS based modulators.

18. A system of claim 1, wherein said exciting unit is configured to activate with light a signal emitting molecule generated by at least one of the biosensing elements while in contact with the sample, resulting in the emission of a response signal, said exciting light being configured to cause single- or multi-photon interaction with the biosensing elements.

19. A system of claim 18, wherein the signal emitting molecule is a luminescence or fluorescence emitting molecules.

20. A method for monitoring multiple samples and/or multiple target agents by monitoring detectable responses generated by a plurality of biosensing elements while in contact with a plurality of samples, respectively, located in an array of spaced-apart sites, the method comprising:

exciting an array of the biosensing elements by an array of exciting signals, each being a pulsed signal having a pulsing frequency differing from that of the other exciting signals, so that each biosensing element of said array is excited by a predefined pulsing frequency different from that of the other biosensing elements, thereby enabling each biosensing element to generate a response signal of a different pulsing frequency;

concurrently receiving the response signals by a single receiving element and generating a single output signal indicative of the received signals; and processing said single output signal based on the different pulsing frequencies of the response signals coming from the different biosensing elements, for identifying in said single output, signal parts corresponding to the response signals coming from the spaced-apart sites, thereby enabling identification of the existence and location of at least one sample and/or target agent, wherein said processing comprises separating said output signal into its Fourier components, and obtaining the signal parts coming from different locations, thereby enabling to identify the location of the responding biosensing element, and monitor its temporal evolution, and comprises applying phase locking to the output signals for identifying different phases for the Fourier components, respectively.

21. The method of claim 20, wherein said exciting signals are light beams of the different pulsing frequencies and a wavelength range capable of causing generation of the optical response signals.

22. The method of claim 21, comprising carrying out at least one of the following: splitting light from a light emitter into said array of spatially separated light beams of substantially the same power and directing them towards the spaced-apart sites, and modulating the pulsing frequencies of the light beams when propagating towards said sites; and directing light from an array of diode lasers towards the array of sites, respectively, while driving the diode lasers to produce the array of pulsed light beams of different pulsing frequencies.

23. The method of claim 21, comprising directing light from an array of diode lasers towards the array of sites, respectively, while driving the diode lasers to produce the array of pulsed light beams of different pulsing frequencies, said exciting light being capable of exciting molecules in the biosensing elements generated in response to the presence of the target agent causing the response light signals therefrom.

24. The method of claim 21, comprising splitting light from a light emitter into said array of spatially separated light beams of substantially the same power and directing them towards the spaced-apart sites, and modulating the pulsing frequencies of the light beams when propagating towards said sites, the light beams being directed towards the sites made in a substrate through a light distributor integrated in said substrate.

25. The method of claim 21, wherein said light beams are in a visible spectrum.

26. The method of claim 21, wherein said exciting light is configured to activate a signal emitting molecule generated by at least one of the biosensing elements while in contact with the sample, said activation being a result of single- or multi-photon interaction of the exciting light with the signal emitting molecule.

27. The method of claim 26, wherein the signal emitting molecule is fluorescence emitting molecule.

28. The method of claim 20, wherein the receiving element is a photomultiplier detector receiving the light signals and generating the single electrical output signal.

29. The method of claim 20, characterized by at least one of the following: (1) the biosensing element in each site differs from the elements in the other sites by its property causing the response signal therefrom; and (2) the biosensing element comprises whole cells selected from bacteria, yeast and protozoa.

30. The method of claim 29, wherein the biosensing element in each site differs from the elements in the other sites by its property causing the response signal therefrom, said property including an ability of creation of a fluorescent molecule in response to the presence of the target agent.

31. A method of fabricating an electro-optical circuit within a KLTN-based material for use in monitoring multiple microbial sensing elements located in respective sites in said structure, the method comprising:

a. bombarding said KLTN-based material with high energy ions to create a cladding layer of partially amorphous material, while controlling the depth of said layer by controlling the energy of said implanted ions and controlling the thickness of said layer high energy ions by controlling the dosage of said implanted ions; and, b. creating in the KLTN crystal a waveguiding layer sandwiched between the crystal surface and the said cladding layer, c. creating at least one optical switching device and at least one electro-optic modulator in said waveguiding layer of KLTN crystal sandwiched between the said cladding layer and the crystal surface, by selective spatial implantation of high energy ions at a predetermined energy.

32. A method for monitoring multiple samples and/or multiple target agents by monitoring detectable responses generated by a plurality of biosensing elements while in contact with a plurality of samples, respectively, located in an array of spaced-apart sites, the method comprising:

splitting light from a light emitter into an array of spatially separated light beams of substantially the same power and directing them towards the spaced-apart sites, and modulating pulsing frequencies of the light beams when propagating towards said sites to thereby create a corresponding array of exciting signals each being a pulsed signal having a pulsing frequency differing from that of the other exciting signals and a wavelength range capable of causing generation of the optical response signals, the light beams being directed towards the sites made in a substrate through a light distributor integrated in said substrate;

exciting an array of the biosensing elements located in said sites by the array of exciting signals, so that each biosensing element of said array is excited by a predefined pulsing frequency different from that of the other biosensing elements, thereby enabling each biosensing element to generate a response signal of a different pulsing frequency;

concurrently receiving the response signals by a single receiving element and generating a single output signal indicative of the received signals; and processing said single output signal based on the different pulsing frequencies of the response signals coming from the different biosensing elements, for identifying in said single output, signal parts corresponding to the response signals coming from the spaced-apart sites, thereby enabling identification of the existence and location of at least one sample and/or target agent.

33. The method of claim 32, wherein said processing comprises separating said output signal into its Fourier components, and obtaining the signal parts coming from different locations, thereby enabling to identify the location of the responding biosensing element, and monitor its temporal evolution.

34. The method of claim 32, wherein said processing comprises applying phase locking to the output signals for identifying different phases for the Fourier components, respectively.

35. The method of claim 32, wherein the receiving element is a photomultiplier detector receiving the light signals and generating the single electrical output signal.

36. The method of claim 32, wherein said light beams are in a visible spectrum.

37. A system for monitoring detectable responses from multiple biosensing elements while in contact with multiple samples present located in an array of spaced-apart sites, the system comprising:

an exciting unit configured and operable for producing an array of exciting signals each comprising a frequency differing from those of the other exciting signals, and exciting a corresponding array of the biosensing elements by said array of signals, respectively, so that each biosensing element of said array is excited by a different exciting signal, thereby enabling each biosensing element to generate a response signal tagged by the different frequency, the exciting unit being an optical unit comprising a light distributor for distributing light of an exciting wavelength range in the form of the array of light beams towards the spaced-apart sites, said exciting signals being light beams of the different pulsing frequencies, the light distributor comprising a power distributor for receiving light from a light emitter, and an optical power grid adapted to controllably direct the exciting light to said sites; and a detection unit comprising a single receiving element associated with said array of biosensing elements and configured for concurrently receiving the multiple response signals and generating a single output signal indicative thereof;

the system being configured and operable to enable to identify, in said single output signal, signal parts corresponding to the response signals of the spatially separated biosensing elements, based on the different frequencies in the response signals coming from the different sites.

38. The system of claim 37, comprising a data processor configured and operable for processing the output signal by separating said signal into its Fourier components, and obtaining the signal parts coming from different locations, thereby enabling to identify the location of the responding biosensing element.

39. The system claim 38, wherein the data processor comprises a phase locking utility configured and operable for identifying different phases of the Fourier components, respectively.

40. The system of claim 37, wherein the optical power grid has at least one of the following configurations: (i) is configured as an arrangement of light guiding elements, interconnected between the power distributor and said sites; (ii) comprises a network of waveguides interconnected by optical switches.

41. The system of claim 37, wherein said exciting unit comprises: an array of modulators which are accommodated in optical paths of said light beams propagating towards said sites and are configured and operable to modulate the light beams with the different pulsing frequencies.

42. The system of claim 41, wherein the modulator includes at least one of the following light modulators: electrooptical, acoustooptical, and MEMS based modulators.

43. The system of claim 37, wherein said light emitter is adapted for generating the exciting light of the wavelength range capable of exciting molecules generated in response to the presence of the target agent in the biosensing elements causing the response light signals therefrom.

44. The system of claim 37, wherein the optical power grid comprises a network of waveguides interconnected by optical switches, said waveguides being operative in a visible spectrum.

45. The system of claim 37, wherein said optical power grid comprises a network of waveguides interconnected by optical switches, and a plurality of optical switching devices located at junctions of the power grid network and configured for performing selective distribution of said exciting light propagating through the waveguides to said sites.

46. The system of claim 45, wherein said optical switching devices are selected from a ring cavity waveguide (RCW) and digital optical switch.

47. The system of claim 37, wherein the optical modulators are installed in predetermined locations within said optical power grid, and are operable for performing temporal modulation of said exciting light.

48. The system of claim 47, wherein said optical modulator comprises an electrooptically controlled Mach-Zender interferometer implemented in a waveguided configuration.

49. A system for monitoring detectable responses from multiple biosensing elements while in contact with multiple samples present located in an array of spaced-apart sites, the system comprising:

an exciting unit configured and operable for producing an array of exciting signals each comprising a frequency differing from those of the other exciting signals, and exciting a corresponding array of the biosensing elements by said array of signals, respectively, so that each biosensing element of said array is excited by a different exciting signal, thereby enabling each biosensing element to generate a response signal tagged by the different frequency, the exciting unit being an optical unit comprising a light distributor for distributing light of an exciting wavelength range in the form of the array of light beams towards the spaced-apart sites, said exciting signals being light beams of the different pulsing frequencies, and comprising an array of modulators which are accommodated in optical paths of said light beams propagating towards said sites and are configured and operable to modulate the light beams with the different pulsing frequencies, the system comprising a substrate formed with said spaced-apart sites for carrying the biosensing elements, said substrate being configured for carrying said light distributor;

a detection unit comprising a single receiving element associated with said array of biosensing elements and configured for concurrently receiving the multiple response signals and generating a single output signal indicative thereof;

the system being configured and operable to enable to identify, in said single output signal, signal parts corresponding to the response signals of the spatially separated biosensing elements, based on the different frequencies in the response signals coming from the different sites.

50. The system of claim 49, wherein said substrate is configured as an electro-optic structure with the light distributor being integral in said substrate.

51. The system of claim 49, wherein the optical modulators are integral in said substrate.

52. The system of claim 49, wherein the light emitter is located outside said substrate.

* * * * *